(12) United States Patent
Goossen et al.

(10) Patent No.: US 9,597,046 B2
(45) Date of Patent: Mar. 21, 2017

(54) METHOD AND DEVICE FOR IMAGING SOFT BODY TISSUE USING X-RAY PROJECTION AND OPTICAL TOMOGRAPHY

(71) Applicant: KONINKLIJKE PHILIPS N.V., Eindhoven (NL)

(72) Inventors: Andre Goossen, Radbruch (DE); Harald Sepp Heese, Hamburg (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 230 days.

(21) Appl. No.: 14/359,967

(22) PCT Filed: Nov. 13, 2012

(86) PCT No.: PCT/IB2012/056382
§ 371 (c)(1),
(2) Date: May 22, 2014

(87) PCT Pub. No.: WO2013/076616
PCT Pub. Date: May 30, 2013

(65) Prior Publication Data
US 2014/0288420 A1    Sep. 25, 2014

Related U.S. Application Data

(60) Provisional application No. 61/563,091, filed on Nov. 23, 2011.

(51) Int. Cl.
*A61B 5/05* (2006.01)
*A61B 6/00* (2006.01)
(Continued)

(52) U.S. Cl.
CPC .......... *A61B 6/4417* (2013.01); *A61B 5/0035* (2013.01); *A61B 5/0073* (2013.01);
(Continued)

(58) Field of Classification Search
CPC ... A61B 6/4417; A61B 5/7425; A61B 5/0035; A61B 6/482; A61B 5/0091;
(Continued)

(56) References Cited

U.S. PATENT DOCUMENTS

2007/0238957 A1* 10/2007 Yared ............... A61B 5/0059
600/407
2007/0244395 A1   10/2007 Wang
(Continued)

FOREIGN PATENT DOCUMENTS

WO    2012080914 A1    6/2012

OTHER PUBLICATIONS

Azar et al: "Standardized Platform for Coregistration of Nonconcurrent Diffuse Opetical Magnetic Resonance Breast Images Obtained in Different Geometries": Journal of Biomedical Optics, vol. 12, No. 5, Jan. 2007, pp. 051902-051902-14.
(Continued)

*Primary Examiner* — Sanjay Cattungal

(57) ABSTRACT

Soft body tissue, such as a female breast, is imaged using X-ray projection techniques and optical tomography techniques. First image data for a first image of a breast (17) are acquired by X-ray projection using an X-ray source (3) and an X-ray detector (5). Second image data for a second image are acquired using optical tomography equipment comprising a light source (9) and a light detector (11). From the first image data, estimated bulk optical properties of the breast (17) are be derived. Based on such estimated bulk optical properties, an optical tomography image is reconstructed from the second image data with high image quality. Per-
(Continued)

forming mammography acquisition at different compression states of the breast (17) improves patient comfort. Mammograms are acquired at two different compression states wherein a first compression state is adapted to provide high image resolution. At a second compression state, another mammogram may be acquired together with an optical tomography image. The two mammograms are used for image registration thereby possibly providing information for a deformation transform. Additional information on tissue composition within the breast is received by acquiring the first and second mammogram at different X-ray settings.

17 Claims, 1 Drawing Sheet

(51) Int. Cl.
A61B 5/00 (2006.01)
A61B 6/04 (2006.01)
(52) U.S. Cl.
CPC .......... *A61B 5/0091* (2013.01); *A61B 5/7425* (2013.01); *A61B 6/463* (2013.01); *A61B 6/482* (2013.01); *A61B 6/502* (2013.01); *A61B 6/5217* (2013.01); *A61B 6/5247* (2013.01); *A61B 6/0414* (2013.01); *A61B 6/54* (2013.01)
(58) Field of Classification Search
CPC ..... A61B 5/0073; A61B 6/463; A61B 6/5217; A61B 6/5247; A61B 6/502; A61B 6/0414; A61B 6/54

USPC .................................. 600/407–430, 473–480
See application file for complete search history.

(56) References Cited

U.S. PATENT DOCUMENTS

| | | | |
|---|---|---|---|
| 2009/0268866 A1* | 10/2009 | Hoheisel | A61B 6/0414 378/37 |
| 2010/0256496 A1* | 10/2010 | Zhu | A61B 5/0091 600/459 |
| 2013/0109963 A1* | 5/2013 | Zhu | A61B 8/0825 600/427 |

OTHER PUBLICATIONS

Chiang et al: "Dual-Direction Measuring System of Near Infrared Optical Tomography Combined With X-Ray Mammography"; MVA2011 Conference on Machine Vision Applications, Jun. 2011, Nara, Japan, pp. 540-543.

Fang et al: "Combined Optical Imaging and Mammography of the Healthy Breast: Optical Contrast Derived From Breast Structure and Compression"; IEEE Transactions on Imaging, vol. 28, No. 1, Jan. 2009, pp. 30-42.

Li et al : "Tomographic Optical Breast Imaging Guided by Three-Dimensional Mammography"; Applied Optics, Sep. 2003, vol. 42. No. 25, pp. 5181-5190.

* cited by examiner

METHOD AND DEVICE FOR IMAGING SOFT BODY TISSUE USING X-RAY PROJECTION AND OPTICAL TOMOGRAPHY

CROSS-REFERENCE TO PRIOR APPLICATIONS

This application is the U.S. National Phase application under 35 U.S.C. §371 of International Application No. PCT/IB2012/056382, filed on Nov. 13, 2012, which claims the benefit of U.S. Provisional Patent Application No. 61/563091, filed on Nov. 23, 2011. These applications are hereby incorporated by reference herein.

FIELD OF THE INVENTION

The present invention relates to a method and a device for imaging soft body tissue such as a female breast. Furthermore, the invention relates to a computer program product for performing such method and a computer-readable medium having stored thereon such computer program product.

BACKGROUND OF THE INVENTION

In order to be able to examine soft body tissue such as a female breast and possibly detect tumourous tissue therein, various imaging methods have been developed.

For example, mammography imaging uses X-rays which are projected through the breast and are detected after transmission such that, from the detected X-ray intensity distribution, information may be derived with respect to geometry and X-ray absorption of structures within the breast. The images acquired by a mammography X-ray projection are typically two-dimensional (2D).

As an alternative imaging technique, optical tomography has been developed. Optical tomography is a type of computer tomography that generates a digital volumetric model of an object by reconstructing three-dimensional images made from light transmitted and scattered through the object. Therein, optical tomography uses the fact that the object is typically at least partially light-transmitting or translucent. Accordingly, these techniques are best suitable for soft tissues such as present in a female breast. For example, in diffuse optical tomography (DOT) light in the near infrared spectrum is transmitted through a soft tissue object and detected after transmission. From data of detected light intensity, information about structural properties and material properties within the soft tissue volume may be derived due to differing diffusive characteristics of various tissue types. For example, information about local concentrations of oxygenated haemoglobin and deoxygenated haemoglobin may be obtained by DOT and such information may allow deriving additional information about functional properties of tissue comprised in a region of interest. Three-dimensional (3D) images may be reconstructed from such acquired optical tomography image data. The spatial resolution of e. g. diffusive optical tomography techniques is typically rather coarse, e.g. in a range of several millimeters.

Qianqian Fang; Carp, S. A.; Selb, J.; Boverman, G.; Quan Zhang; Kopans, D. B.; Moore, R. H.; Miller, E. L.; Brooks, D. H.; Boas, D. A.; , "Combined Optical Imaging and Mammography of the Healthy Breast: Optical Contrast Derived From Breast Structure and Compression," Medical Imaging, IEEE Transactions on , vol. 28, no. 1, pp. 30-42, January 2009 doi: 10.1109/TMI.2008.925082 discloses combined X-ray mammography/diffusive optical breast imaging. However, the proposed approach still suffers from shortcomings concerning e.g. image quality and/or patient comfort.

SUMMARY OF THE INVENTION

There may be a need e.g. for a method of imaging soft body tissue such as a female breast and for a device implementing such method allowing improved visualization of structures and tissue characteristics occurring within a region of interest of the soft body tissue. Particularly, there may be e.g. a need for an imaging method and device providing information on soft body tissue characteristics at high spatial resolution. Furthermore, there may be a need for a computer program product adapted for implementing such method on a computer and for a computer-readable medium having stored thereon such computer program product.

At some of the needs resulting from shortcomings of prior art approaches may be met by the subject-matter of the independent claims. Further embodiments of the invention are defined in the dependent claims.

According to a first aspect of the present invention, a method of imaging a soft body tissue is proposed to comprise the following steps: (a) acquiring first image data for a first image of a region of interest of the soft body tissue using X-ray projection; (b) acquiring second image data for a second image of the region of interest of the soft body tissue using optical tomography; (c) deriving estimated bulk optical properties of the soft body tissue in the region of interest from the acquired first image data; and (d) reconstructing the second image from the second image data using the derived estimated bulk optical properties.

The method steps can be performed in a different order than indicated. For example, the order of steps (a) and (b) may be inversed.

A general idea underlying the first aspect of the invention may be seen in realizing synergy effects by acquiring image data using two different types of imaging, i. e. X-ray projection imaging and optical tomography imaging, wherein not only the advantages of each of the imaging techniques are combined but further advantageous effects may be achieved.

For example, benefit may be taken from the fact that first image data acquired using X-ray projection may provide for two-dimensional images representing X-ray absorption characteristics of the radiographed soft body tissue at high spatial resolution. From such first image data an estimation of optical properties in the bulk of the soft body tissue may be derived. Such information may subsequently be used to improve the reconstruction of a second image from second image data acquired using optical tomography techniques. Typically, such second image reconstruction may be complex and may suffer from inaccuracies as in such reconstruction specific assumptions generally have to be taken before initiating the reconstruction. The determination of such assumptions is generally complicated and may result in inaccuracies in the reconstructed image. Inter alia, such assumptions may relate to bulk optical properties present in the soft body tissue to be imaged using optical tomography as such bulk optical properties may influence the transmission and diffusion of light used for the optical tomography imaging.

It is proposed herein to provide a high quality estimate for such bulk optical properties by deriving estimated bulk optical properties of the soft body tissue from previously acquired X-ray projection image data allowing deriving bulk optical properties at high spatial resolution. Using such estimated bulk optical properties, the reconstruction of the optical tomography image may be improved and may, inter alia, show increased spatial resolution.

Embodiments of the proposed method may be specifically used for imaging a female breast. The first image data may then be acquired using mammography X-ray projection and the first image may also be referred to as a mammogram. In such imaging of a female breast, the second image data may be advantageously acquired using diffused optical tomography (DOT). DOT may provide for a three-dimensional image including functional information about the tissue comprised in a region of interest.

The proposed imaging method may further comprise an additional process step of acquiring third image data for a third image of the region of interest of the soft body tissue using X-ray projection. Therein, the first image data is acquired with the soft body tissue being in a first compression state and the second and third image data is acquired with the soft body tissue being in a different second compression state at lower compression than in the first compression state.

The acquisition of third image data may further improve the reconstruction of the second image acquired by optical tomography. Particularly, it may be beneficial to acquire first image data of e. g. a female breast at high compression of the breast and, additionally, acquire third image data at lower compression of the breast, both image data being acquired using X-ray projection. While, at high compression of the breasts, a mammogram of high quality and high information content may be acquired, the high compression may be uncomfortable for the patient. As optical tomography requires relatively long illumination periods, the second image data using optical tomography may be acquired at lower compression of the breast thereby considerably improving comfort of the patient. In order to better correlate the first image data and the second image data, these first and second image data being acquired using different imaging techniques and at different compression states, third image data are further acquired, these third image data being acquired with the same technique as the first image data and at the same compression state as the second image data.

For example, the first image data and the third image data may be elastically registered to one another. Thereby, a so-called "deformation prior" relating to the first and second compression state of the breast may be derived. This deformation prior may comprise information about how the examined soft body tissue is deformed between the first compression state and the second compression state. Such information may be advantageously used in subsequently reconstructing the second image from the second image data.

For example, bulk estimated optical properties of the soft body tissue derived from the first image data, being acquired at high compression, may be transformed using the information contained in the transformation prior. The second image may then be reconstructed from the second image data, acquired at low compression, while additionally using such transformed bulk optical properties.

In other words, bulk optical properties may first be estimated by deriving information from the first image data which have been acquired with X-ray projection at high compression of the soft body tissue and therefore comprise high resolution detailed structural information about local absorption in the soft body tissue. Then, in order to improve the patient's comfort, the compression of the soft body tissue may be reduced and second and third image data may be acquired using optical tomography and using X-ray projection, respectively. The high quality information comprised in the first image data may then be used for estimating bulk optical properties. In principle, such bulk optical properties could also be derived from the third image data, acquired at lower compression, but with lower information quality as X-ray projection at such lower compression typically results in images having lower spatial resolution and/or less information about local X-ray absorption. Therefore, the detailed information on bulk optical properties derived from the first image data is to be used and is then transformed to the geometry of the soft body tissue taken in the second lower compression state. Therein, the information obtained by registering the first image data and the third image data, both being acquired with X-ray projection but in different compression states, may be used as deformation prior in transforming the estimated bulk optical properties which have previously been derived from the high quality first image data. Thus, the information about the bulk optical properties is maintained at high quality but is transformed into the geometry which is taken by the soft body tissue in the second compression state at which also the second image data is acquired using optical tomography. Accordingly, the second image may finally be reconstructed at high quality from the second image data using such transformed bulk optical properties.

In the proposed method, the first image data may be acquired with a first setting for X-ray energy, X-ray spectrum and/or X-ray dose and the third image data may be acquired with a different second setting for X-ray energy, X-ray spectrum and/or X-ray dose.

In such embodiment, benefit may be taken from the fact that soft body tissue may have different X-ray absorption characteristics at different settings for the radiation used for the X-ray projection. In other words, a specific type of soft body tissue may have different X-ray absorption characteristics at different X-ray energy, X-ray spectrum and/or x-ray dose than another type of soft body tissue. Accordingly, by using different settings for the X-ray radiation used in acquiring the first image data and third image data, respectively, additional information on the local distribution of tissue types in the soft body tissue may be acquired.

For example, estimated information on tissue composition of the soft body tissue in the region of interest may be derived taking into account the acquired first image data and the acquired third image data. Subsequently, estimated bulk optical properties of the soft body tissue in the region of interest may be derived from the estimated information on tissue composition. Finally, the second image may be reconstructed from the second image data using such estimated bulk optical properties.

Accordingly, in such embodiment, estimated bulk optical properties may be derived not only based on a single data acquisition with X-ray projection, i.e. the first image data, but on two data acquisitions using X-ray projection at different X-ray settings. From these two image data, additional information may be derived, such additional information relating to tissue composition in the region of interest of the soft body tissue. As the optical properties within the region of interest may, inter alia, depend on the local tissue composition, this additional information may then be used for a more precise estimate of the bulk optical properties in the region of interest. Such improved estimate may result in enabling improved reconstruction of the second image, i.e. the optical tomography image.

The reconstructed second image may be displayed together with the first image. Both images may relate to different information content. For example, the second image may comprise information on physiological functions within the soft body tissue whereas the first image may comprise detailed geometrical information on structures within the soft body tissue.

The first and second images may be displayed as a registered superposition of a two-dimensional second image derived from the reconstructed three-dimensional second image and of the two-dimensional first image.

Therein, the 2D second image may e.g. be derived from the reconstructed 3D second image for example by calculating a 2D projection through the 3D second image with respect to an imaging plane corresponding to the imaging plane at which the first image is acquired by X-ray projection. Alternatively, the 2D second image may e.g. be derived from the reconstructed 3D second image for example by calculating a 2D slice of the 3D second image in a plane parallel to the imaging plane at which the first image is acquired.

While the first and second 2D images may be acquired at different compression states of the soft body tissue and may therefore relate to different geometrical states of the region of interest in the soft body tissue, these two 2D images may be superpositioned after registering the images. The registration may comprise a transformation of the first 2D image, acquired in a first geometrical state of the soft body tissue at high compression, to a second geometrical state of the soft body tissue at low compression at which the second image data have been acquired, or vice versa. After such transformation, both 2D images may be superpositioned and displayed to the user, thereby enabling simplified image analysis by the user.

According to a further aspect of the present invention, an imaging device is proposed. This imaging device is adapted for performing embodiments of the above-identified imaging method.

For example, the imaging device may comprise a soft body tissue compressor for compressing the soft body tissue at different compression states. Furthermore, an X-ray source and an X-ray detector arranged on opposite sides of the soft body tissue compressor as well as an optical tomography light source and an optical tomography light detector arranged on opposite sides of the soft body tissue compressor, are provided. Furthermore, a computer adapted to performing the above-defined method in one of its embodiments is comprised in the imaging device.

The imaging device may be adapted to automatically control at least one of the soft body tissue compressors, the X-ray source, the X-ray detector, the optical tomography light source and the optical tomography light detector.

Accordingly, the imaging device may be adapted to automatically acquire first, second and, optionally, third image data using a respective means for X-ray projection and optical tomography, respectively, and, possibly, bringing the soft body tissue to specific different compression states using the soft body tissue compressor.

According to a third aspect of the present invention, a computer program product is proposed to comprise computer-readable instructions for instructing a computer to perform a method according to an embodiment of the above-identified method. Such computer program product may be stored on a computer-readable medium. The computer program product may use computer-readable instructions in any suitable programming language to acquire image data from respective imaging means, process such data and finally output such data for e.g. visualization. The computer-readable medium may be any type of medium adapted for storing computer-readable instructions such as e.g. CDs, DVDs, flash memory, etc.

It has to be noted that aspects and embodiments of the present invention and possible features and advantages thereof are described herein with reference to different subject-matters. In particular, some embodiments are described with reference to method type claims whereas other embodiments are described with reference to device type claims. However, a person skilled in the art will understand from the above and the following description that, unless other notified, in addition to any combination of features belonging to one type of subject-matter also any combination between features relating to different subject-matters, in particular between features of the device type claims and features of the method type claims, is considered to be disclosed with this application.

BRIEF DESCRIPTION OF THE DRAWINGS

Embodiments of the present invention are described in the following with reference to the enclosed figures. Neither the description nor the figures shall be interpreted as limiting the invention.

The figures are only schematically and not to scale.

DETAILED DESCRIPTION OF EMBODIMENTS

Figure 1:
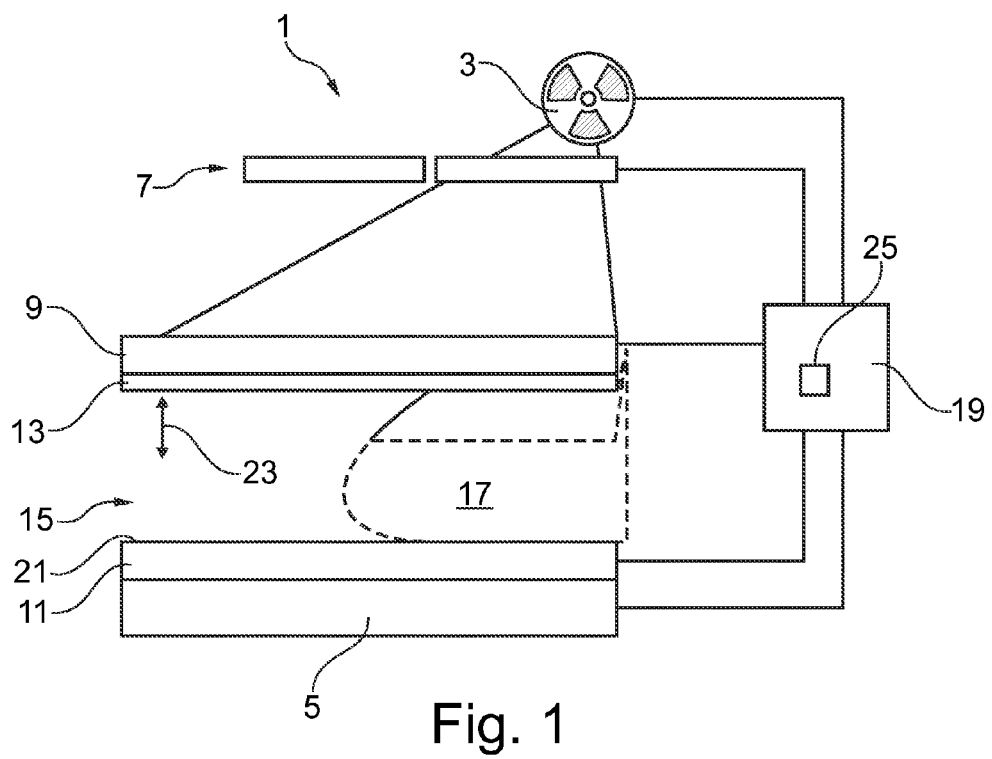
FIG. 1 shows an imaging device according to an embodiment of the present invention.

FIG. 1 shows an imaging device 1 which may be used for performing an imaging method according to embodiments of the present invention as described in further detail below. The imaging device 1 is adapted for imaging a female breast 17 at different compression states and with different imaging modalities.

The imaging device 1 comprises a soft body tissue compressor 15 having a compression paddle 13 which may be moved in a vertical direction 23 as indicated in FIG. 1. Using the movable compression paddle 13, a female breast 17 interposed between the compression paddle 13 and a housing 21 may be compressed to different compression states as schematically indicated in the figure by dotted and solid lines, respectively.

An X-ray source 3 and an X-ray detector 5 are arranged at opposite sides of the compressor 15. The X-ray source 3 may emit X-rays towards a region of interest within the breast 17 such that these X-rays are transmitted through the region of interest and are subsequently detected by the X-ray detector 5. Accordingly, mammography X-ray projections may be acquired.

The X-ray source 3 may be operated at different operating conditions such as e.g. different acceleration voltages, electron flow densities, etc., such that an energy, a spectrum and/or a dose of X-rays emitted by the X-ray source 3 may be varied. Furthermore, filters 7 may be introduced into an X-ray beam and may be dynamically exchangeable. By establishing such different settings during X-ray image data acquisition, characteristics of the X-rays emitted from the X-ray source 3 may be specifically adapted such that different types of body tissue show differing X-ray absorption characteristics depending on the X-ray absorptions such that, finally, information on the tissue composition within the region of interest may be acquired with high precision.

Additionally to the components 3, 5, 7 of the radiography equipment, components of optical tomography equipment may be arranged adjacent to the breast 17. An optical tomography light source 9 may be arranged on top of the transparent compression paddle 13 and an optical tomography light detector 11 may be arranged underneath the breast 17, for example within the housing 21 which may also be transparent to light emitted by the optical tomography light source 9.

The optical tomography light source 9 comprises a multiplicity of individual light emitters at different locations such that light, for example in the near infrared (NIR) spectral range, may be emitted towards the breast 17 and transmitted through the breast 17 at different angles towards the optical tomography light detector 11. The optical tomography light detector 11 comprises a multiplicity of individual light detectors distributed in a matrix such that light transmitted through the breast 17 and possibly diffused therein may be two-dimensionally detected. By acquiring a multiplicity of two-dimensional images using the optical tomography light detector 11 upon light transmission through the breast at different angles, a three-dimensional optical tomography image may be reconstructed. In a beneficial setup, various lights sources may be combined to obtain varying patterns of light emission which may be detected by all sensors. This may yield quasi-angular information which may be subsequently used for image reconstruction. Accordingly, there may be no need for mechanical movement of components of the DOT equipment during the DOT acquisition.

All components of the imaging device 1, i.e. the X-ray source 3, the X-ray detector 5, the filters 7, the optical tomography light source 9, the optical tomography light detector 11 and a moving mechanism (not shown) for the movable compression paddle 13 of the compressor 15 are connected to a control 19. This control 19 may control and operate the components automatically and acquire, process and output data from the components in order to perform an imaging method according to an embodiment of the present invention as described in the following.

First, the female breast is arranged on top of the housing 21 and underneath the compression paddle 13. By lowering the compression paddle 13 along the direction 23, the breast 17 is compressed to a first compression state as indicated by the dotted line in FIG. 1.

In such first compression state, first image data of the breast 17 are acquired by projecting X-rays from the X-ray source 3 through the breast 17 towards the X-ray detector 5 and detecting the transmitted X-rays by the detector 5. For such mammography X-ray projection, standard settings for X-ray energy, X-ray spectrum, X-ray dose and the selection of the filter material 7 may be used.

Subsequently, the compression to the breast 17 is reduced by moving the compression paddle 17 upwards. Thereby, a second compression state of the breast 17 as indicated in FIG. 1 by the solid line may be obtained.

In such second compression state, another mammogram is acquired. In other words, third image data of the region of interest of the breast 17 are acquired by X-ray projection. In such X-ray projection at the second compression state of reduced compression, different settings for the X-ray source 3 and/or the filters 7 may be used. For example, an acceleration voltage of the X-ray source 3 may be increased and an electron flow density may be reduced and the filter introduced into the X-ray beam may be exchanged such that the third image data are acquired with high X-ray photon energy at low-dose.

Then, the optical tomography light source 9 and the optical tomography light detector 11 may be arranged adjacent to the breast 17 while keeping the breast 17 in the second compression state. Using this optical tomography equipment 9, 11, second image data of the region of interest of the breast 17 are acquired.

After such image data acquisition, the breast 17 may be released from the compressor 15. Optionally, the procedure may be repeated for the second breast.

Figure 2:
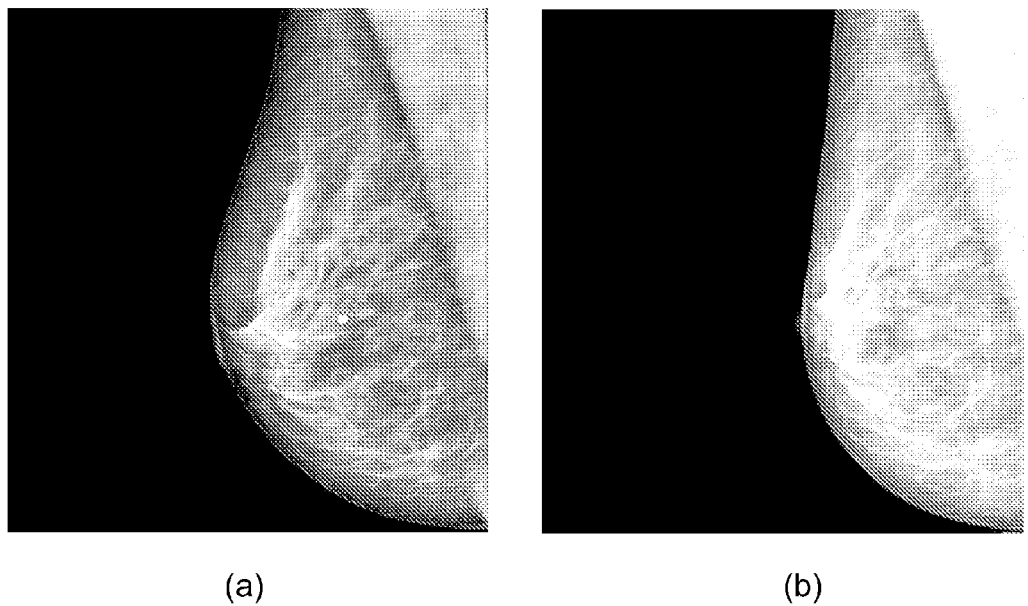
FIGS. 2(a), (b) show mammograms acquired at normal and reduced compression.

FIG. 2(*a*) shows a mammogram of the breast 17 in the first high compression state. FIG. 2(*b*) shows a mammogram in the second low compression state. It may be clearly seen that in the mammogram of the first high compression state, more details are visible.

All the image data may be acquired by the detectors 5, 11, respectively, as digital data and may be transferred to a computer 25 comprised in the control 19. The computer 25 is adapted for acquiring the first, second and third image data and processing these data.

For example, the computer 25 may derive an estimation of bulk optical properties of the breast 17 from the acquired first image data and use such estimated bulk optical properties in order to improve reconstruction of the second image, i.e. a three-dimensional optical tomography image, from the second image data.

In a preferred embodiment, the computer 25 performs an elastic registration of the two acquired mammograms, i.e. the first image and the third image, in order to thereby derive information for a deformation prior relating to the first and second compression states of the breast 17.

Furthermore, the computer 25 may analyze a tissue composition of soft body tissue within the breast 17 based on breast density and dual energy spectral decomposition. Therein, information on tissue composition of the breast in the region of interest may be derived by taking into account the first image data and the third image data acquired at different X-ray settings and analyzing differences between these first and third image data. Details on possible dual-energy volumetric breast density assessment may be derived from European application No. 10194750.5.

Such estimated information on tissue composition may be subsequently used in reconstructing the second image from the second image data as such information on tissue composition may serve for more precisely estimating bulk optical properties of the breast in the region of interest. Accordingly, this information may be used for more accurate volume of interest definition as initialization for optical tomography reconstruction. Therein, the volume of interest definition may not be linked to tissue composition, but can be derived directly from the high spatial resolution of the third image data alone. It is important to mention that there is no deformation between second and third image data.

Finally, the computer 25 may process the acquired image data for displaying a registered superposition of a two-dimensional image derived from the reconstructed second image and of a first image. In other words, the local distribution of functional data as derived from the second image data of the optical tomography image acquisition and the structural data as derived from the first mammography image may be registered and superpositioned. In order to obtain a registered overlay of the structural data from the mammogram acquired at normal compression and standard dose and the optical tomography measurement acquired at reduced compression, information comprised in the deformation prior as derived by elastically registering the first and third image data may be used. Finally, the overlaid first and second image may be visualized as a fused image. Such visualization may be presented to a user, for example on a display or may be printed out.

As such visualized fused image comprises both structural features at high resolution from the mammogram and functional features from the optical tomography image and, as furthermore, the optical tomography image is of high quality as a result of using additional information derived from the mammogram, such fused image may provide valuable information to a physician in order to detect for example cancerous tissue within the breast.

Finally, possible features, functions and advantages of embodiments of the present invention may be summarized in a different wording as follows.

Multimodal fusion of diffuse optical tomography (DOT) and mammography promises to overcome deficiencies of both imaging modalities by drawing on the strength of each thereby possibly enabling synergy effects. Functional information with a spatial resolution in the range of 10 millimeters is provided by optical properties and high resolution structural image contrast is generated using X-rays with spatial resolution of possibly less than 0.1 millimeters. The DOT measurement may be integrated with a mammography system.

However, DOT requires a lengthy measurement acquisition that may add up to the acquisition time for a mammogram.

In order to improve patient comfort, it is desirable to perform DOT at reduced breast compression.

This may introduce a correspondence problem between the result of the DOT measurement and the mammogram, and may require an estimation of a deformation field. Furthermore, DOT may be sensitive to an estimation of bulk optical properties in order to correctly interpret the measured response. Existing techniques with optical cameras are only able to capture external deformation without information about the internal structures of the breast. In addition, it may be hard to determine optical properties accurately from a single mammogram without precise knowledge about compression height.

In other words, main disadvantages of combined mammography and DOT acquisitions are long measurement times. Reduced breast compression may improve the patient comfort but introduces a correspondence problem: Mammograms have to be acquired at normal compression in order to achieve sufficient visibility of structures for diagnostic purpose; DOT measurements are performed at reduced compression because of the long measurement time, but they lack structural contrast and only provide functional responses at a coarse resolution.

According to embodiments of the invention, such correspondence problem may be overcome by using a deformation prior derived from the registration of two mammograms.

Furthermore, the use of a single two-dimensional mammogram to estimate bulk optical properties for DOT normalization may be disadvantageous. Extracting tissue fractions from mammograms may be highly susceptible to inaccurate compression height estimation and therefore error-prone. According to embodiments of the invention, such disadvantage may be overcome by complementing a first mammogram with a dual energy pendant at reduced compression.

According to embodiments, the invention proposes a method to fuse a digital mammogram with the result of a diffuse optical tomography (DOT) at a different breast compression. DOT typically only provides coarse resolution and requires structural information of a complementary modality in order to allow spatial evaluation of the data. Furthermore, DOT depends on estimated bulk optical properties, i.e. different tissue types within the volume of interest, in order to normalize the response. To improve patient comfort during a lengthy DOT acquisition, it is desirable to perform it at reduced breast compression. However, mammographic image quality may strongly depend on a high breast compression. Thus, it is proposed to acquire an additional low-dose radiograph at reduced compression using different filter and/or energy settings for X-ray acquisition.

According to embodiments of the invention, an additional low-dose mammogram is exploited at the same reduced compression as used for an optical tomography image acquisition. Using a deformable registration scheme, it may be possible to derive a smooth deformation field containing correspondences between pixels in the mammogram acquired at normal compression and the follow-up acquisition at reduced compression. These correspondences also connect DOT and radiographic image data and thus allow an accurate overlay of functional and structural image content.

To improve an estimation of bulk optical properties from the mammogram(s) for normalization of the DOT results, it may be possible to acquire the second mammogram with different photon energy, target material and/or filter material. With such a dual energy approach, relevant structures for a registration would still be visible within the mammogram on the one hand and the decomposition of the breast into different tissue types can be performed more robustly using the two complementary energies, compared to tissue type decomposition estimation from a single mammogram. Moreover, high spatial resolution of the mammogram acquired at the same compression level as the DOT acquisition may allow for more accurate definition of a volume of interest for DOT reconstruction.

It should be noted that the term "comprising" does not exclude other elements or steps and that the indefinite article "a" or "an" does not exclude the plural. Also elements described in association with different embodiments may be combined. It should also be noted that reference signs in the claims shall not be construed as limiting the scope of the claims.

LIST OF REFERENCE SIGNS 1 imaging device
3 X-ray source
5 X-ray detector
7 exchangeable filters
9 optical tomography light source
11 optical tomography light detector
13 compression paddle
15 soft body tissue compressor
17 breast
19 control
21 housing
23 moving direction
25 computer

The invention claimed is:

1. A method of imaging a soft body tissue, the method comprising:
acquiring first image data for a first image of a region of interest of the soft body tissue using X-ray projection;
acquiring second image data for a second image of the region of interest of the soft body tissue using optical tomography;
deriving estimated bulk optical properties of the soft body tissue in the region of interest from the acquired first image data;

reconstructing the second image from the second image data using the estimated bulk optical, properties; and
acquiring third image data for a third image of the region of interest of the soft body tissue using X-ray projection, wherein the first image data is acquired with the soft body tissue being in a first compression state and the second and third image data is acquired with the soft body tissue being in a different second compression state at lower compression than in the first compression state.

2. The method of claim 1, further comprising:
elastically registering the first image data and the third image data thereby deriving a transform relating the first and second compression states of the soft body tissue.

3. The method of claim 2, further comprising:
transforming the estimated bulk optical properties using the transform; and
reconstructing the second image from the second image data additionally using such transformed estimated bulk optical properties.

4. The method of claim 1,
wherein the first image data is acquired with a first setting for X-ray energy, X-ray spectrum and/or X-ray dose, and
wherein the third image data is acquired with a different second setting for X-ray energy, X-ray spectrum and/or X-ray dose.

5. The method of claim 4, further comprising:
deriving estimated information on tissue composition of the soft body tissue in the region of interest taking into account the acquired first image data and the acquired third image data;
deriving the estimated bulk optical properties of the soft body tissue in the region of interest from the estimated information on tissue composition; and
reconstructing the second image from the second image data using such estimated bulk optical properties.

6. The method of claim 1, wherein the second image data is acquired using diffuse optical tomography.

7. The method of claim 1, further comprising:
displaying a registered superposition of a 2-dimensional image derived from the reconstructed second image and the first image.

8. An imaging device, comprising:
a soft body tissue compressor for compressing a soft body tissue to at least two different compression states;
an X-ray source and an X-ray detector arranged at opposite sides of the soft body tissue compressor;
an optical tomography light source and an optical tomography light detector arranged at opposite sides of the soft body tissue compressor; and
at least one computer configured to perform the method according to claim 1.

9. The imaging device of claim 8, wherein the device is adapted to automatically control at least one of the soft body tissue compressor, the X-ray source, the X-ray detector, the optical tomography light source and the optical tomography light detector.

10. A non-transitory computer readable medium having stored thereon computer readable instructions for instructing a computer to perform the method according to claim 1.

11. A method of imaging breast tissue, the method comprising:
compressing a breast to a first compression state;
with the breast in the first compression state, generating first image data of the breast;
compressing the breast to a second compression state, the second compression state being less compressed than the first compression state;
with the breast in the second compression state, generating second image data using optical tomography and generating third image data;
with at least one processor, determining a transform relating the first compression state and the second compression state based on the first and third image data;
with the at least one processor, derive estimated bulk optical properties of the breast from the first image data and transform the estimation of the bulk optical properties to the second compression state with the determined transform;
with the at least one processor, reconstructing an optical tomographic image of the breast from the second image data and the transformed estimation of the bulk optical properties; and
displaying the optical diagnostic image on a display device.

12. The method according to claim 11, wherein the first and third image data include X-ray projection image data, the first and third image data being generated with different X-ray settings, and further including:
with the at least one processor, performing a dual-energy volumetric breast density assessment based on the first and third image data.

13. The method according to claim 12, wherein the soft tissue includes a breast.

14. The method according to claim 11, further including:
with the at least one processor, combining the optical tomographic image with an image generated from one of the first and third image data; and
displaying the combined image on the display device.

15. An imaging apparatus for imaging soft body tissue, the apparatus comprising:
a compression device including at least one compression panel configured for compressing a soft tissue to a first compression state and to a second compression state, the second compression state being less compressed than the first compression state;
an X-ray imaging system configured to:
with the soft tissue in the first compression state, generating first image data of the soft tissue, and
with the soft tissue in the second compression state, generating third image data,
an optical imaging system configured to generate second image data;
at least one processor configured to:
determine a transform relating the first compression state and the second compression state based on the first and third image data,
derive estimated bulk optical properties of the soft tissue from the first image data,
reconstruct an optical tomographic image of the soft tissue based on the second image data, the transform, and the estimated bulk optical properties; and
a display device configured to display the optical tomographic image.

16. The apparatus according to claim 15, wherein the at least one processor is further configured to:
perform a dual-energy volumetric breast density assessment based on the first and third image data.

17. The apparatus according to claim 15, wherein the at least one processor is further configured to:

combine the optical tomographic image with an image generated from one of the first and third image data and display the combined image on the display device.

\* \* \* \* \*